US005468562A

United States Patent [19]
Farivar et al.

[11] Patent Number: 5,468,562
[45] Date of Patent: Nov. 21, 1995

[54] METALLIZED POLYMERIC IMPLANT WITH ION EMBEDDED COATING

[75] Inventors: Mohammad Farivar, Chestnut Hill; Piran Sioshansi, Lincoln, both of Mass.

[73] Assignee: Spire Corporation, Bedford, Mass.

[21] Appl. No.: 195,824

[22] Filed: Feb. 10, 1994

Related U.S. Application Data

[60] Continuation of Ser. No. 6,749, Jan. 21, 1993, abandoned, which is a division of Ser. No. 663,361, Mar. 1, 1991, abandoned.

[51] Int. Cl.$^6$ ................................................. B32B 9/00
[52] U.S. Cl. .................. 428/457; 428/35.7; 428/35.8; 428/35.1; 428/34.7; 604/264; 604/265; 604/280; 604/905
[58] Field of Search ................................. 428/457, 461, 428/434, 465, 460, 35.7, 35.8, 35.1, 34.7, 458, 209; 604/265, 268, 266, 264, 905

[56] References Cited

U.S. PATENT DOCUMENTS

| | | | |
|---|---|---|---|
| 3,557,795 | 1/1971 | Hirsch | 128/335.5 |
| 3,589,975 | 6/1971 | Andrews et al. | 161/165 |
| 3,695,921 | 10/1972 | Shepherd et al. | 117/72 |
| 3,699,956 | 10/1972 | Kitrilakis et al. | 128/348 |
| 4,027,393 | 1/1977 | Ellis . | |
| 4,039,699 | 8/1977 | Morimoto et al. | 427/38 |
| 4,152,478 | 5/1979 | Takagi | 428/221 |
| 4,253,463 | 3/1981 | Kim | 604/280 |
| 4,281,029 | 7/1981 | Takagi et al. | 427/38 |
| 4,374,717 | 2/1983 | Drauglis et al. | 427/40 |
| 4,388,164 | 6/1983 | Kolev et al. | 427/40 |
| 4,411,648 | 10/1983 | Davis et al. | 604/21 |
| 4,440,108 | 4/1984 | Little et al. | 118/719 |
| 4,443,488 | 4/1984 | Little et al. | 427/38 |
| 4,452,827 | 6/1984 | Kolev et al. | 427/38 |
| 4,476,590 | 10/1984 | Scales et al. | 3/1.91 |
| 4,479,795 | 10/1984 | Mustacich et al. | 604/53 |

(List continued on next page.)

FOREIGN PATENT DOCUMENTS

| | | |
|---|---|---|
| 0029787 | of 0000 | European Pat. Off. . |
| 206024A | of 0000 | European Pat. Off. . |
| 86107598 | 12/1986 | European Pat. Off. . |
| 87307136 | 3/1988 | European Pat. Off. . |
| 3228849A | of 0000 | Germany . |
| 3302567 | 7/1984 | Germany ........................ 604/280 |
| 3830359 | 12/1989 | Germany ........................ 623/11 |
| 91/00453 | 7/1992 | WIPO . |
| 92/08266 | 4/1993 | WIPO . |
| 93/00685 | 8/1993 | WIPO . |
| 93/00201 | 11/1993 | WIPO . |

OTHER PUBLICATIONS

Maki et al. (Dec. 1973) "Infection Control in Intravenous Therapy", *Ann. Int. Med.*, 79:867–887.

Tully et al. (Mar. 1981) "Complications of Intravenous Therapy with Steel Needles and Teflon® Catheters", *Am. J. Med.*, 70:702–706.

Falchuk et al. (1984) "Microparticulate–Induced Phlebitis", *N.E. J. Med.*, 312:78–82.

(List continued on next page.)

*Primary Examiner*—Patrick J. Ryan
*Assistant Examiner*—Patrick Jewik
*Attorney, Agent, or Firm*—Thomas J. Engellenner; John V. Bianco; Lahive & Cockfield

[57] ABSTRACT

Surface metallized polymeric implants, such as cannula, needles, catheters, connectors and the like, a dry coating method therefor and apparatus to accomplish the same are disclosed. The metallization of the implants is intended to improve their biocompatibility and to reduce infusion-associated phlebitis and infection. The method essentially includes the dry coating of the outside surfaces of the polymeric implants with a metallic thin film. The apparatus to effect the dry coating method essentially includes a vacuum chamber, an evaporator and an ion source mounted in operative association within the chamber, and means for rotatably mounting a plurality of polymeric implants for exposure to the evaporator and the ion source.

6 Claims, 4 Drawing Sheets

U.S. PATENT DOCUMENTS

| | | | |
|---|---|---|---|
| 4,581,028 | 4/1986 | Fox, Jr. et al. | 623/2 |
| 4,592,920 | 6/1986 | Murtfeldt | 427/2 |
| 4,592,926 | 6/1986 | Murtfeldt | 604/280 |
| 4,683,149 | 7/1987 | Suruki et al. | 427/38 |
| 4,693,760 | 9/1987 | Sioshansi | 148/4 |
| 4,718,905 | 1/1988 | Freeman | 427/2 |
| 4,743,308 | 5/1988 | Sioshansi et al. | 148/4 |
| 4,743,493 | 5/1988 | Sioshansi et al. | 428/217 |
| 4,846,834 | 7/1989 | von Recum et al. | 427/2 |
| 4,855,026 | 8/1989 | Sioshansi | 204/192.11 |
| 4,871,366 | 10/1989 | von Recum et al. | 623/11 |
| 4,872,922 | 10/1989 | Bunker et al. | 148/4 |
| 4,886,505 | 12/1989 | Haynes et al. | 604/265 |
| 4,923,450 | 5/1990 | Maeda et al. | 604/265 |
| 4,936,281 | 6/1990 | Stasz | 128/660.03 |
| 4,994,060 | 2/1991 | Rink et al. | 606/28 |
| 5,049,140 | 9/1991 | Brenner et al. | 604/266 |
| 5,057,106 | 10/1991 | Kasevich et al. | 606/33 |
| 5,067,491 | 11/1991 | Taylor, II et al. | 128/748 |
| 5,069,227 | 12/1991 | Maronian | 427/2 |
| 5,165,952 | 11/1992 | Solomon et al. | 427/2 |
| 5,223,309 | 6/1993 | Farivar | 427/525 |
| 5,236,509 | 8/1993 | Sioshansi et al. | 118/719 |
| 5,308,704 | 5/1994 | Suzuki et al. | 427/525 |

OTHER PUBLICATIONS

Lewis et al. (1985) "Assessment of thromboresistance of intravenous cannulae by $^{125}$I–fibrinogen scanning", *J. Biomed. Mat. Res.*, 19:99–113.

Power et al. (Jul. 1986) "Fatal Bacterial Endocarditis as a Complication of Permanent Indwelling Catheters", *Am. J. Med.*, 81:166–168.

Elliott (May 1988) "Intravascular–device infections", *J. Med. Microbiol.*, 27:161–167.

Bentivegna (Aug. 1989) "The Vitacuff and Intravascular Catheter–Related Infection", *JAMA Letters*, 262:613–614.

Liedberg et al. (Jan. 1989) "Assessment of Silver–Coated Urinary Catheter Toxicity by Cell Culture" *Urol. Reg.*, 17:359–360.

Solnick–Legg et al. (Apr. 1989) "Ion Beam and Plasma Technology for Improved Biocompatible Surfaces", MRS BULLETIN, pp. 27–30.

Johnson et al. (Nov. 1990) "Prevention of Catheter–Associated Urinary Tract Infection with a Silver Oxide–Coated Urinary Catheter: Clinical and Microbiologic Correlates", *J. Infect. Dis.*, 162:1145–1150.

Liedberg et al. (1990) "Silver Alloy Coated Catheters Reduce Catheter–Associated Bacteriuria", *Brit. J. Urol.*, 65:379–381.

Putterman (1990) "Central venous catheter related sepsis: A clinical review", *Resuscitation,* 20:1–16.

Haywood "Dual IBAD Makes Good Coatings", *Advanced Materials and Processes*, vol. 138, Issue 6, publication of The Materials Information Society, (Feb. 6, 1991).

Mahan et al. (Mar. 1991) "Factors in Pin Tract Infections", *Orthopedics*, 14:305–308.

Murphy et al. (Mar. 1991) "The Small Pin Circular Fixator For Proximal Tibial Fractures With Soft Tissue Compromise", *Orthopedics*, 14:273–280.

IBAD Brochure, Spire Corporation, Bedford, Mass., published Mar. 8, 1991.

SPI–ARGENT™ Brochure, published Oct. 9, 1992.

SPI–ARGENT™ Technical Brochure, published Apr. 23, 1993.

Solmick–Legg et al. "Ion Beam and Plasma Technology for Improved Biocompatible Surface," *MRS BULLETIN*, Apr. 1987 pp. 27–3.

METALLIZED POLYMERIC IMPLANT WITH ION EMBEDDED COATING

This application is a file wrapper continuation of U.S. application Ser. No. 08/006,749, filed on Jan. 21, 1993 now abandoned, which is a division of application Ser. No. 07/663,361 filed on Mar. 1, 1991 now abandoned.

BACKGROUND OF THE INVENTION

1. Field of the invention

The present invention relates generally to polymeric implants and, more particularly, to surface metallized polymeric implants so as to improve their biocompatibility, a dry coating method and an apparatus for effecting the metallization.

2. The Prior Art

Fluid replacement and administration of drugs and nutrients by the intravenous route have become an integral part of patient care. It has been estimated that over one-fourth of patients hospitalized in the U.S.A. receive intravenous infusions for one reason or another. The introduction of plastic catheters in 1945 was enthusiastically received for delivering intravenous fluids. Polymers have good bulk properties, such as flexibility. Plastic catheters also are less expensive to make than are steel needles. Hence, many medical device manufacturers prefer using polymeric materials for making implants, such as cannula, needles, catheters, percutaneous connectors and the like. "Cannula" is a general term used in the medical devices field that includes all types of plastic catheters, percutaneous devices, draining tubes and steel needles. The use of polymeric implants, however, has brought with it alarming reports of complications, especially thrombophlebitis and sepsis. See Dennis G. Maki, M.D., et al "Infection Control in Intravenous Therapy," *Annals of Internal Medicine* 79:867–887, 1973; J. Lewis et al "Assessment of Thromboresistance of Intravenous Cannulae by $^{125}$I-Fibrinogen Scanning," *Journal of Biomedical Materials Research*, Vol. 19, 99–113 (1985); Mario L. Corona, M.D. et al "Infections Related to Central Venous Catheters," *Mayo Clinic Proc.* July 1990, Vo. 65.

Some workers in the field have investigated the use and the beneficial effect of an in-line filter in reducing infusion-associated infection, in particular phlebitis, see Kenneth H. Falchuk, M.D., et al "Microparticulate-Induced Phlebitis," *The New England Journal of Medicine*, Vol. 312, No. 2, Jan. 10, 1985, 78–82. Others have, however, focused on the material of the cannula itself. See Gerald Friedland, M.D., "Infusion-Related Phlebitis—Is the In-Line Filter the Solution?" *The New England Journal of Medicine*, Vol. 312, No. 2, Jan 10, 1985, 113–115; and John L. Tully, M.D. et al "Complications of Intravenous Therapy with Steel Needles and TEFLON® Catheters—A Comparative Study," *The American Journal of Medicine*, Vol. 70, March 1981, 702–706. Amongst others, the latter two articles conclude that steel needles produce fewer infusion-associated complications, such as phlebitis than do plastic cannulae. And therein lies the knob of the problem—how to use advantageously the desirable bulk property of polymeric implants, to wit, flexibility, avoiding infiltration without adversely affecting the patient by exposing him to increased risk of infusion-associated plebitis and infection?

The common assignee herein, Spire Corporation of Bedford, Massachusetts, has been one of the pioneers in the field of ion beam technology. A plasma-supported ion beam technique for coating industrial cutting tools with a thin layer of cubic boron nitride to improve the tools' cutting properties is disclosed in U.S. Pat. No. 4,440,108, of Roger G. Little et al, granted Apr. 3, 1984, and assigned to said Spire Corporation. A plasma-ion deposition process of large-grain, thin semiconductor films directly on low-cost amorphous substrates is disclosed in U.S. Pat. No. 4,443,488, also of Roger G. Little et al, granted Apr. 17, 1984 and assigned to said Spire Corporation. A process of preventing surface discoloration in titanium orthopaedic implants by ion implantation is disclosed in U.S. Pat. No. 4,693,760 of Piran Sioshansi, granted Sep. 15, 1987 and assigned to said Spire Corporation. An ion implantation process for plastics to enhance their surface hardness and their resistance to chemical attack is disclosed in U.S. Pat. No. 4,743,493 of Piran Sioshansi et al, granted May 10, 1988 and assigned to said Spire Corporation. A process for passivating the electrochemically active surface of metal alloys so as to inhibit their corrosion is disclosed in U.S. Pat. No. 4,743,308 of Piran Sloshansi et al, granted May 10, 1988 and assigned to said Spire Corporation. A sputter-enhanced ion implantation process, primarily of ball bearings, without the use of a separate evaporation system is disclosed in U.S. Pat. No. 4,855,026 of Piran Sioshansi, granted Aug. 8, 1989 and assigned to said Spire Corporation. An improved method and apparatus for the uniform ion implantation of spherical surfaces, such as ball bearings, is disclosed in U.S. Pat. No. 4,872,922 of Stephen N. Bunker et al, granted Oct. 10, 1989 and assigned to said Spire Corporation. A method of depositing an ionized cluster on a substrate is disclosed in U.S. Pat. No. 4,152,478 of Toshinori Takagi, granted May 1, 1979. And a method of coating a substrate with a stoichiometric compound is disclosed in U.S. Pat. No. 4,281,029 of Toshinori Takagi et al, granted Jul. 28, 1981. The use of ion beam processing is thus well known and widespread.

SUMMARY OF THE INVENTION

It is a principal object of the present invention to overcome the above disadvantages by providing polymeric implants that combine the advantageous properties of biocompatible metals with the advantageous bulk properties of polymers and, by providing processes and apparatus to effect the same.

More specifically, it is an object of the present invention to provide surface metallized polymeric implants, such as cannula, needles, catheters, percutaneous connectors and the like that combine to advantage the respective desirable properties of each, i.e., the flexibility of polymers and the biocompatibility of metals, and to provide processes and apparatus for effecting the metallization of the polymeric implants.

The dry coating process of the invention essentially includes providing an implant formed of a polymeric material, introducing the polymeric implant in a vacuum chamber system provided with both an ion source and an evaporator, and forming a thin metallic film on the surface of the polymeric implant. Preferably, the thin metallic film is formed by an ion beam process, such as an ion beam assisted deposition process or by sputtering. The apparatus for rendering polymeric implants biocompatible by dry coating their surfaces with a thin metallic film essentially comprises a vacuum chamber, an ion source and an evaporator operatively mounted within the chamber, means to expose a plurality of implants to both the ion source and the evaporator within the chamber so as to dry coat the surface thereof, means to effect a negative pressure within the chamber, and power means to operate the operative parts of the apparatus.

Preferably, the means to expose the plurality of implants includes a substrate holder rotatably mounted within the chamber. Preferably, a thickness monitor is disposed within the chamber to monitor for uniformity in application and for thickness in the thin metallic film being deposited on the surfaces of the polymeric implants. Preferably, the ion source is a bucket type ion source.

Other objects of the present invention will in part be obvious and will in part appear hereinafter.

The invention accordingly comprises the surface metallized polymeric implants and the process and the apparatus of effecting such surface metallization of the present disclosure, its steps, components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

Figure 1:
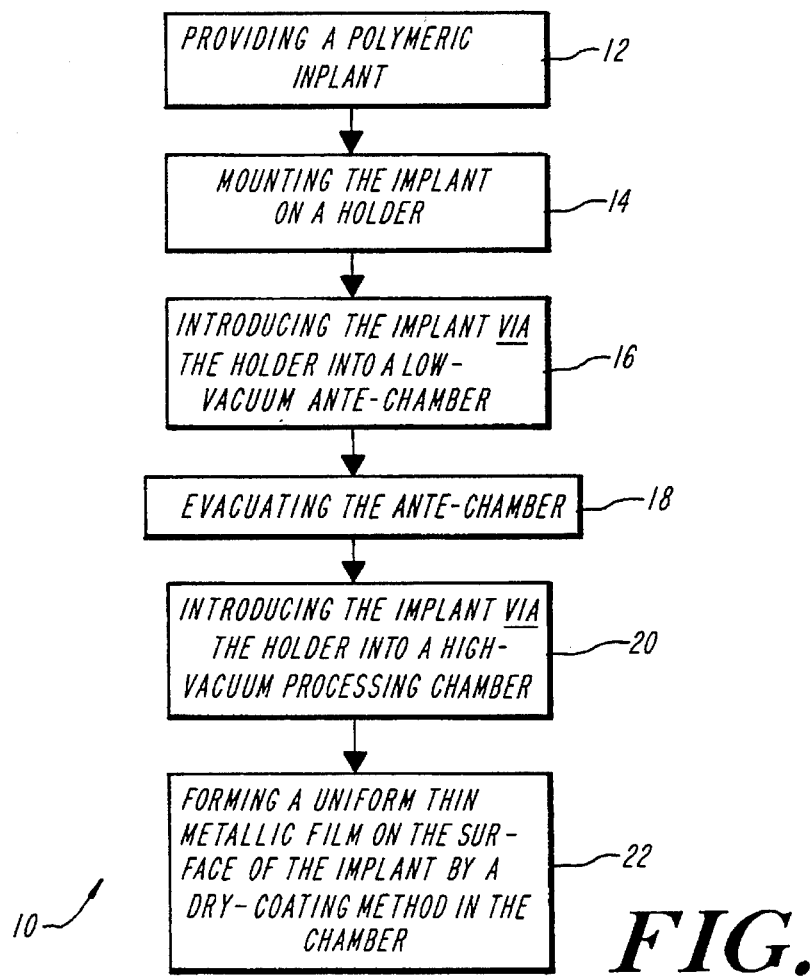
FIG. 1 is a flow diagram of a preferred process of the invention.

In general, the present invention relates to surface metallized polymeric implants, such as cannulae, catheters, percutaneous connectors and the like, so as to make such implants biocompatible, thereby reducing infusion-associated phlebitis and infection, and metal associated infiltrations occassioned by their use and yet retain the advantageous bulk properties of polymers, such as their flexibility, and a process and an apparatus for effecting such surface metallization.

As stated, fluid replacement and administration of drugs and nutrients by the intravenous route have become an integral part of patient care. Medical device manufacturers and many practitioners prefer making and using polymeric implants because of their desirable bulk properties, such as flexibility. The use of such polymeric implants has not been without problems, however. There have been widespread and alarming reports of complications, especially thrombophlebitis and sepsis, accompanying the use of polymeric implants. Investigators have found that microorganisms adhere to the plastic surface by electrostatic forces and/or by chemical and mechanical means. These investigators have observed that coagulase-negative staphylococci produce a polysaccharide or "slime" substance, which acts as an agent that bonds the microorganisms to the catheter. This slime substance acts as a physical barrier and also serves to inhibit the immune response as an antiopsonic molecule. A rough surface, as opposed to a smooth one, of the catheter causes increased attachment of microorganisms and a predisposition to thrombosis, which in turn further promotes colonization. For example, the adherence of coagulase-negative staphylococci is greater to a catheter formed of polyvinychtoride (PVC) then it is to one formed of the much smoother TEFLON®.

One worker in the field defined three stages of attachment of microorganisms to central vascular catheters: stage 1=attraction of organisms to the catheter, a process influenced by chemical properties of the surface; stage 2= attachment which is influenced by physicochemical forces and factors such as production of glycocalix and formation of thrombus; and stage 3=multiplication of organisms, influenced by suitability of growing conditions and nutrients. See T. S. J Elliot, "Intravascular-device infections," *J. Med Microbiol* 27:161–167, 1988. Polymeric catheters also may be colonized by means of seeding through the blood from distant sites of infection. Such distant seeding appears to be more common for yeast than it is for *S. aureus*. Enteric bacteria, such as enterococci, *Escherichia coli* and Klebsiella also may infect polymeric catheters by hematogenous seeding.

There appears to be a general consensus among medical practitioners that metallic cannulae cause fewer infusion-associated infections and phlebitis than do plastic cannulae Metallic catheters do not "give," i.e., flex and bend, however, as polymeric catheters do. Thus, metallic needles are apt to puncture the blood vessels, spilling the fluid into the surrounding tissue, known as "infiltration," an occurrence that may result in various unwarranted complications. On the other hand, metallic cannulae exhibit a lower bacterial colonization rate than do plastic PTFE-(i.e. TEFLON®) coated cannulae (41.2% vs. 49%), they also have a lower incidence of septicemia (2.1% vs. 3.4%), and a more significantly lower rate of phlebitis (25% vs. 56%). Phlebitis and cellulitis represent but the onset of infusion-associated infections. They are likely to be followed by fever, sepsis, infiltration, bacteremia, septic thrombophlebitis, disseminated infection and septicemia. Vascular prostheses and artificial surfaces used in cardio-pulmonary bypass and renal dialysis systems are frequently associated with thromboembolic complications due to the polymeric materials employed in such systems since the use of metallic cannulae is not ideal for such applications. It is to alleviate the problems associated with the use of polymeric cannulae and yet keep the benefits of plastics, most notably their flexibility, that is addressed herein by providing biocompatible metallic surfaces on polymeric implants, including a process and an apparatus for effecting the same.

A flow diagram 10 of a preferred process of providing a biocompatible metallized surface to polymeric implants according to the invention is shown in FIG. 1. This process essentially comprises the steps of providing 12 a polymeric implant, mounting 14 the implant on a substrate holder, introducing 16 the implant via the substrate holder into a low-vacuum antechamber, evacuating 18 the low-vacuum antechamber to a high vacuum, further introducing 20 the implant via the substrate holder into a high-vacuum processing chamber, and forming 22 a uniform thin metallic film on the surface of the polymeric implant by a dry coating method within the high-vacuum processing chamber. Preferably, the dry coating method is an ion-beam process, such as an ion beam assisted deposition (IBAD) process or a sputtering process. Ion beam processes are low-temperature, high-technology processes with excellent quality control to achieve good reproducibility, reliability and thickness of deposition control at a high throughput and with no chemical residues, thus being both environmentally and occupationally a safe, dependable technique.

Figure 2:
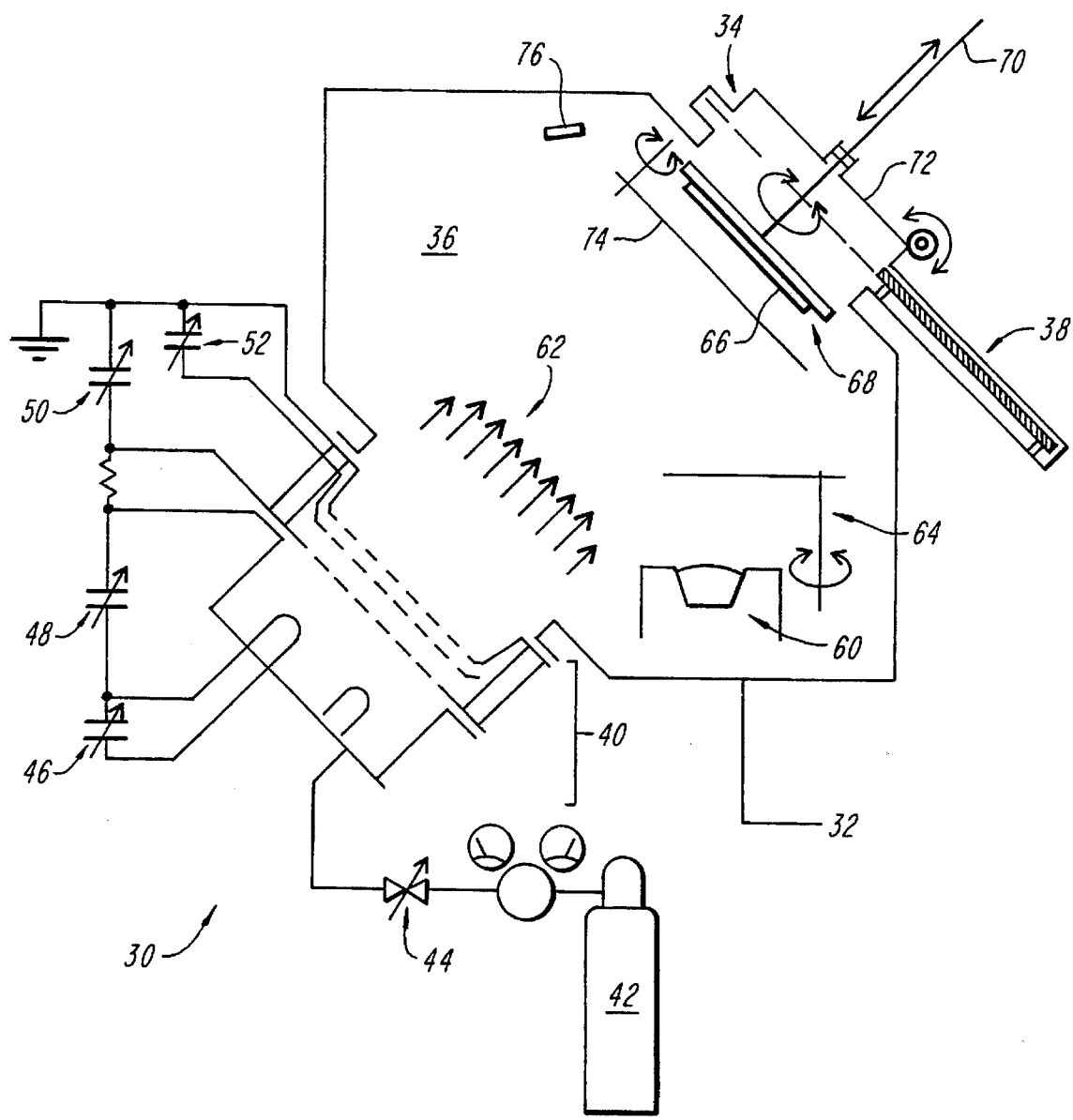
FIG. 2 is a schematic diagram of a preferred apparatus for practicing the process of the invention.

A schematic diagram of a preferred apparatus 30 for practicing the above-described process of the invention is illustrated in FIG. 2.

The apparatus 30 designed for rendering polymeric implants biocompatible, such as cannula, needles, catheters, percutaneous connectors, fluid delivery and removal tubes, and the like, essentially comprises a vacuum chamber system 32 formed of a low-vacuum antechamber 34 and a high vacuum processing chamber 36, air-tightly separated from each other by a gate 38 movable between a shown open position and a closed position shown in dashed lines.

An ion source 40, preferably a bucket type ion source, is mounted within the high-vacuum processing chamber 36 in a position diametrically opposed to the low-vacuum antechamber 34, substantially as shown. As known, the source 40 of ions is fed by one or more gases, such as argon, neon and/or helium, from a suitable gas supply source 42, via a mass flow controller 44, regulating the rate of gas feed. A filament power supply 46 is provided to supply current to the filaments, an arc supply 48 to maintain an arc discharge between the anode and the filaments, an exit power supply 50 to accelerate the ions through the accelerator grid of the multiple grid system of the bucket type ion source 40, and a suppressor power supply 52 for negatively biasing the suppressor grid of the ion source 40 to reduce backstreaming of secondary electrons from the substrate.

An evaporator 60 also is mounted in the high-vacuum processor chamber 36 in operative association with the ion source 40. The evaporator 60 is designed to vaporize particular metallic evaporants so as to dry-coat a specific substrate therewith, being assisted in the dry-coating by an ion beam 62 emanating from the ion source 40. Metallic evaporants include chromium, zirconium, aluminum, nickel, tungsten, molybdenum, tantalum, titanium, platinum, carbon, iridium, gold and silver. A vapor shutter 64, designed to be rotated in and out of place of the evaporator 60, shields the substrates from the evaporants when in place. Substrates 66 to be dry-coated are introduced into the vacuum chamber system 32 of the dry-coating apparatus 30 with the aid of a suitable substrate holder 68. Preferably, the substrate holder 68 is mounted for both rotational and translatory motion on a shaft 70 and is introduced into the antechamber 34 through a hinge-like mounted end-plate 72. A pivotable shutter 74 is provided to shield the substrates 66 from the ion beam 62, when desired. A thickness monitor 76 preferably is provided in operative association with the substrate holder 68 to monitor the thickness of the thin metallic film being deposited on the substrate 68 during operation of the dry-coating apparatus 30.

Figure 3:
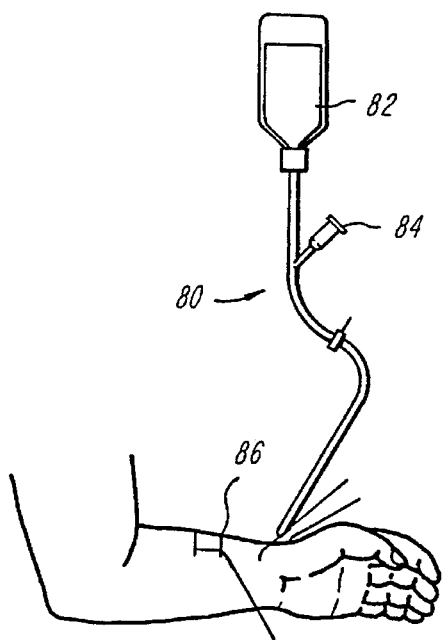
FIG. 3 is a schematic illustration of a typical intravenous infusion system in use.
Figure 4:
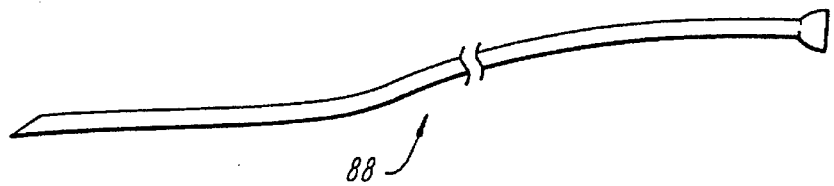
FIG. 4 illustrates a typical polymeric cannula for use in cardiovascular monitoring of a patient.
Figure 6:
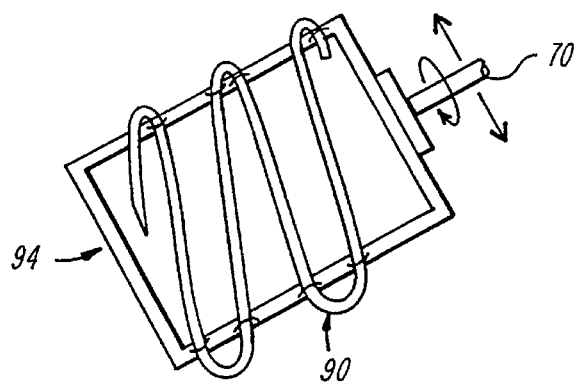
FIG. 6 is a view similar to FIG. 5 but illustrates the dry coating of a full length polymeric catheter according to the invention.

In FIG. 3, a typical intravenous (I.V.) infusion system 80 is shown in operative use admitting a fluid 82 into an arm of a patient. If desired, other substances also can be added to the fluid 82 via a hypodermic needle 84 connected to the I.V. system 80. In this I.V. system 80, only the cannula 86 thereof is inserted into the vascular system of the patient. Hence only this cannula 86 portion of the system 80 need to be dry-coated with the thin metallic film according to the invention. Other catheters 88 and 90, such as illustrated in FIGS. 4 and 6, are designed to be inserted substantially along their axial lengths, however, such as cardiac catheters and pulmonary artery catheters. Some of such catheters are formed with more than one lumen.

Figure 5:
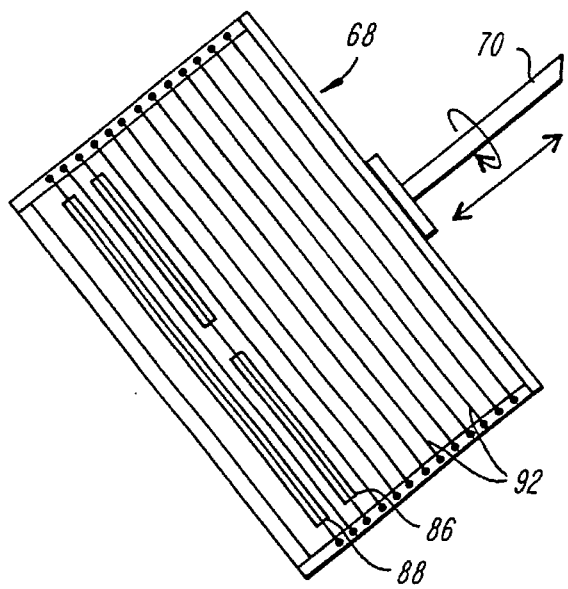
FIG. 5 is a schematic illustration of a modified part of the apparatus shown in FIG. 2, illustrating the dry coating of a plurality of polymeric catheters according to the invention.

The dry-coating of polymeric catheter tips 86 and catheters 88 is illustrated in FIG. 5. As may be observed, the substrate holder 68 is formed as a cage, which is lengthwise adjustable and is lengthwise provided with a plurality of mandrils 92 to accommodate and securely hold a plurality of catheter tips 86 and catheters 88 respectively thereon. The subtrate holder 68 preferably is rotated during the coating operation and is designed to be moved in translation between the antechamber 34 and the high-vacuum processing chamber 36 prior to the coating operation.

The dry-coating of the entire length of a rather long polymeric catheter 90 is illustrated in FIG. 6. A square frame 94 is shown being mounted to the end of the shaft 70. Depending on the relative sizes of the catheter 90 versus the frame 94, one or more catheters 90 are loosely wound about the frame 94. Longer catheters or a number of catheters can be processed on larger frames 94.

Figure 7:
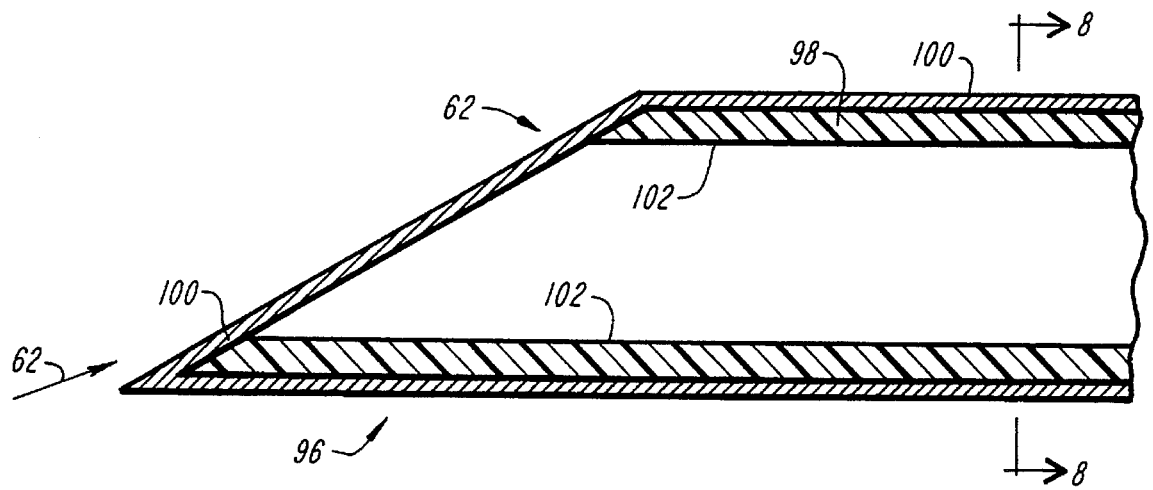
FIG. 7 is a longitudinal cross section, on an enlarged scale, of a polymeric catheter tip dry coated according to the invention.
Figure 8:
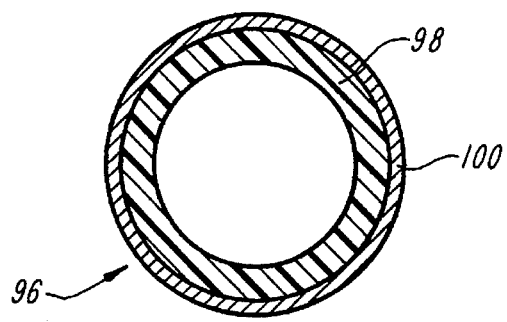
FIG. 8 is a section of the catheter tip shown in FIG. 7 in the direction of the arrows 8—8.

A polymeric catheter tip 96, dry-coated according to the invention and on an enlarged scale, is illustrated in section in FIGS. 7 and 8. The dry-coated polymeric catheter tip 96 comprises a polymeric catheter tip 98, coated on its outside surface as well as on its front beveled end with a metallic thin film 100. It will be observed that a small section on the inside front surface of the polymeric catheter tip 98 also is coated with a thin metallic film 102. It is to be pointed out that the thin metallic film 100 on the outside of the polymeric catheter tip 98 is of even thickness from about 0.5 microns to about ten (10) microns, whereas the thin metallic film 102 on the inside of the tip 98 is tapered and usually does not extend beyond the widest angle of the ion beam 62, as illustrated.

The thin metallic coatings 100 are not only of uniform thickness circumferentially and along the axial length of the catheter tip 98, the coatings also are characterized by being dense, free of pinholes, strongly adherent, hard yet flexible, clean and free of contaminants. Due to the ion beam assisted process, the desired thickness of the metallic coatings 100 is precisely controllable and adjustable, is reliable and reproducible. The dry-coating method, furthermore is environmentally safe, with no chemical residue being produced as a consequence of the process.

EXAMPLE I

A polymeric catheter type 86 has been dry-coated in the apparatus 30 and in accord with the inventive process with the following operational parameters:

Evaporant: Chromium

Ion Beam: Argon

Thickness of Thin Metallic Film Deposited: 0.5 micron

Processing Time: one hour

Vacuum Pressure in Processing Chamber: $10^{-6}$ torr

EXAMPLE II

A polymeric catheter 90 has been dry-coated over its entire length in the apparatus 30 and in accord with the inventive process, employing the following operational parameters:

Evaporant: Titanium

Ion Beam: Argon

Thickness of Thin Metallic Film Deposited: 0.5 micron

Processing Time: one hour

Vacuum Pressure in Processing Chamber: $10^{-6}$ torr

Thus it has been shown and described a surface metallized polymeric implant, a dry-coating method and apparatus to effect the same, which product, process and apparatus satisfy the objects and advantages set forth above.

Since certain changes may be made in the present disclosure without departing from the scope of the present invention, it is intended that all matter described in the accompanying drawings, be interpreted in an illustrative and not in a limiting sense.

What is claimed is:

1. A biomedical device capable of insertion within a subject, the device formed from a unitary flexible polymeric material having an outer surface, the outer surface being coated with an infection reducing material by ion beam assisted deposition, wherein the coating includes atoms of the infection reducing material embedded in the outer surface only partially through the polymeric material to a predetermined depth from the outer surface, and wherein the coating is a substantially uniform, dry coating having a thickness extending outward from the outer surface of between about 0.5 microns and about 10 microns.

2. The biomedical device of claim 1 wherein the infection reducing material comprises a metal.

3. The biomedical device of claim 2 wherein the metal comprises at least one of silver, zirconium, tantalum, carbon, chromium, aluminum, nickel, tungsten, molybdenum, platinum, iridium, gold and stainless steel.

4. The biomedical device of claim 1 wherein the polymeric material comprises at least one of polyurethane, polyethylene, silicone, polytetrafluoroethylene, polyvinyl chloride and polysulfide.

5. The biomedical device of claim 1 wherein the device is one of a catheter, a percutaneous connector, a fluid delivery tube, and a fluid removal tube.

6. The biomedical device of claim, 1 wherein the device is a tubular structure having an outer surface, the outer surface being at least partially coated with the infection reducing material by the ion beam assisted deposition.

* * * * *